United States Patent [19]

Smith, Jr.

[11] Patent Number: 4,545,680
[45] Date of Patent: Oct. 8, 1985

[54] SPECTROANALYSIS SYSTEM

[75] Inventor: Stanley B. Smith, Jr., Westford, Mass.

[73] Assignee: Allied Corporation, Morristown, N.J.

[21] Appl. No.: 483,111

[22] Filed: Apr. 8, 1983

[51] Int. Cl.$^4$ .................... G01J 3/18; G01J 3/42
[52] U.S. Cl. .................... 356/319; 356/334; 356/315
[58] Field of Search .............. 356/307, 313, 315, 319, 356/331, 332, 334

[56] References Cited

U.S. PATENT DOCUMENTS

| | | | |
|---|---|---|---|
| 2,750,836 | 6/1956 | Fastie | 356/332 |
| 2,975,669 | 3/1961 | Jarrell et al. | 356/305 |
| 3,102,155 | 8/1963 | Vallee | 88/14 |
| 3,229,563 | 1/1966 | De Mey | 88/14 |
| 3,247,759 | 4/1966 | Saunderson | 356/313 |
| 3,503,686 | 3/1970 | Walsh | 356/85 |
| 3,508,813 | 4/1970 | Smith, Jr. et al. | 356/87 |
| 3,586,441 | 6/1971 | Smith et al. | 350/275 |
| 3,645,629 | 2/1972 | Dagnall | 356/85 |
| 3,689,158 | 9/1972 | Shifrin | 356/315 |
| 3,735,565 | 5/1973 | Gilby et al. | 356/319 |
| 3,825,344 | 7/1974 | Bonne | 356/85 |
| 3,924,950 | 12/1975 | Siegler, Jr. | 356/307 |
| 3,937,576 | 2/1976 | Schmider | 356/74 |

FOREIGN PATENT DOCUMENTS 1103320 2/1968 United Kingdom ............... 356/307

OTHER PUBLICATIONS

Perkin-Elmer Models 290B and 303 Atomic Absorption Spectrophotometers, Nov. 22, 1968 (brochure).
Fastie, W. G., "Image Forming Properties of the Ebert Monochromator," *Journal of the Optical Society of America*, V. 42, No. 9, p. 649.

*Primary Examiner*—F. L. Evans
*Assistant Examiner*—Joel L. Harringa

[57] ABSTRACT

A chopperless spectroanalytical system of the double beam type in which radiation from a common source is split into reference and analysis beams. The two beams are directed along similar paths such that the analysis beam passes through an analysis region and the reference beam bypasses that analysis region. A monochromator has two spaced aperture regions such that one aperture region provides an entrance aperture for the analysis beam and an exit aperture for a dispersed portion of the reference beam; and the other aperture region provides an entrance aperture for the reference beam and an exit aperture for a dispersed portion of the analysis beam. The beams exiting from the two exit apertures are simultaneously monitored and compared to compensate for errors due to source fluctuations and the like.

18 Claims, 4 Drawing Figures

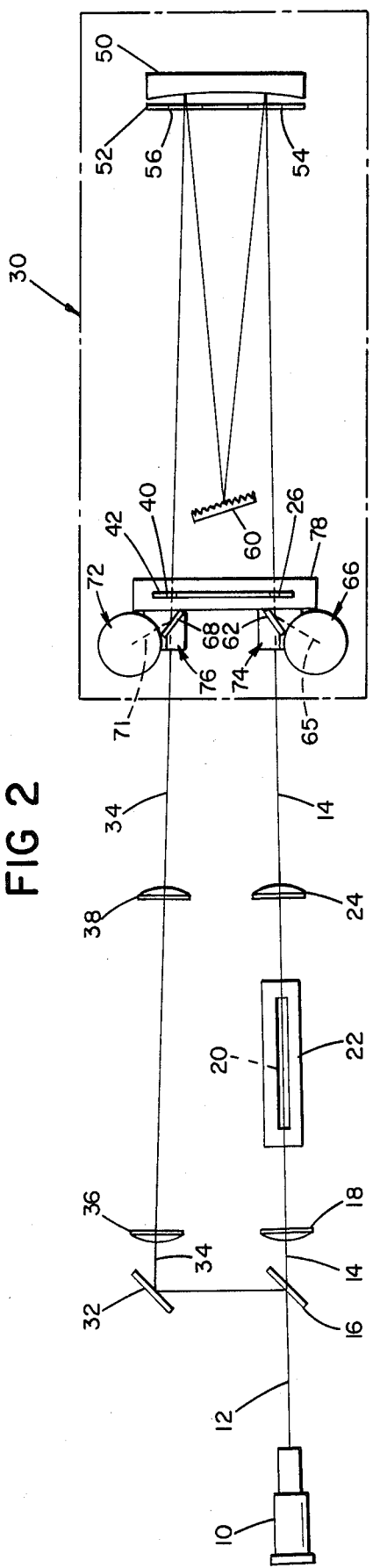
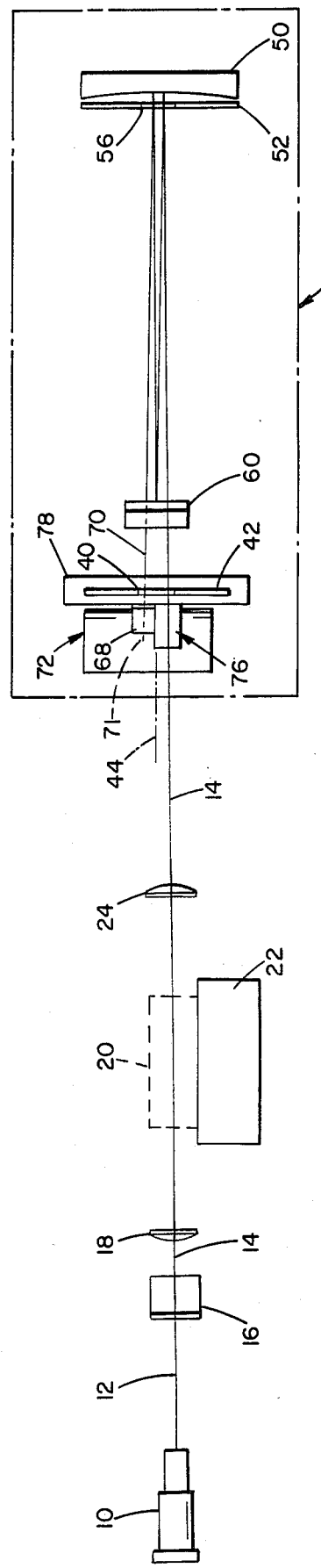
FIG 2
FIG 3

SPECTROANALYSIS SYSTEM

This invention relates to spectroanalysis systems and more particularly to spectroanalysis systems of the double beam type.

In spectroanalysis systems of the double beam type, two beams of radiation are provided, an analysis beam that is modified by the sample to be analyzed and a reference beam that is not modified by the sample. By comparing signals from the reference and analysis beams while making measurements, errors that arise from fluctuations in source intensity are largely eliminated. Frequently, a moving component such as a chopper is used to alternately close and open the two beam channels at a steady rate, a common type of chopper being a rotating shutter. Such a chopper alternately provides radiation along the reference and analysis paths such that there cannot be simultaneous measurement of the two beams which makes difficult to analyze transient events. Also, with such a device, there is an edge interval in which each radiation beam is partially blocked and therefore that interval cannot be used for analytical purposes. Complexities are introduced by the addition of this moving component as the chopper mirror must be flat and precisely positioned relative to the axis of rotation of the chopper and to the beam axis or monochromator system axis. The chopper may be used with a beam splitter or two choppers which are accurately synchronized may be used. The use of movable members in spectroanalytical systems frequently results in loss of accuracy over a period of time.

In accordance with the invention there is provided a spectroanalytical system of the double beam type in which radiation from a common source is split into reference and analysis beams. The two beams are directed along similar paths such that the analysis beam passes through an analysis region and the reference beam bypasses that analysis region. A monochromator is arranged with two spaced aperture regions such that one portion of one aperture region functions as an entrance aperture for the analysis beam and another portion of that aperture region functions as an exit aperture for a dispersed portion of the reference beam, and one portion of the other aperture region functions as an entrance aperture for the reference beam and another portion of that other aperture region functions as an exit aperture for a dispersed portion of the analysis beam. The beams exiting from the two exit apertures may be concurrently monitored and compared to compensate for errors due to source fluctuations and the like.

In a particular embodiment, a hollow cathode type radiation source is employed in an atomic absorption type of analysis system, the output beam from the source is divided by a beam splitter into reference and analysis beams that are passed along generally parallel paths that lie in a plane that is angularly offset from the monochromator axis less than one degree. While separate entrance and exit apertures may be employed, in that particular embodiment the apertures are defined by spaced elongated curved slits of a monchromator of the stigmatic type. The analysis beam passes through the lower portion of one slit and is dispersed into a spectrum with a portion of the dispersed spectrum being passed as an exit beam through the upper portion of the second slit. Similarly, the reference beam passes through the lower portion of the second slit and is dispersed into a spectrum with a portion of the dispersed spectrum of the reference beam being passed as an exit beam through the upper portion of the first slit. The monochromator includes a masked collimating mirror and a reflection grating, and a mirror and detector assembly is supported at each slit for sensing the dispersed radiation exiting through that slit.

The invention thus provides a spectroanalytical system of the double beam type in which a mechanical chopper need not be used. Other features and advantages will be seen as the following description of a particular embodiment progresses, in conjunction with the drawings in which:

FIG. 2 is a diagrammatic plan view of the spectroanalysis system shown in FIG. 1;

FIG. 3 is a diagrammatic elevational view corresponding to the plan view of FIG. 2 and showing the analysis beam path, the reference beam detector 66 and its support being omitted from that diagram.

DESCRIPTION OF PARTICULAR EMBODIMENT

Figure 1:
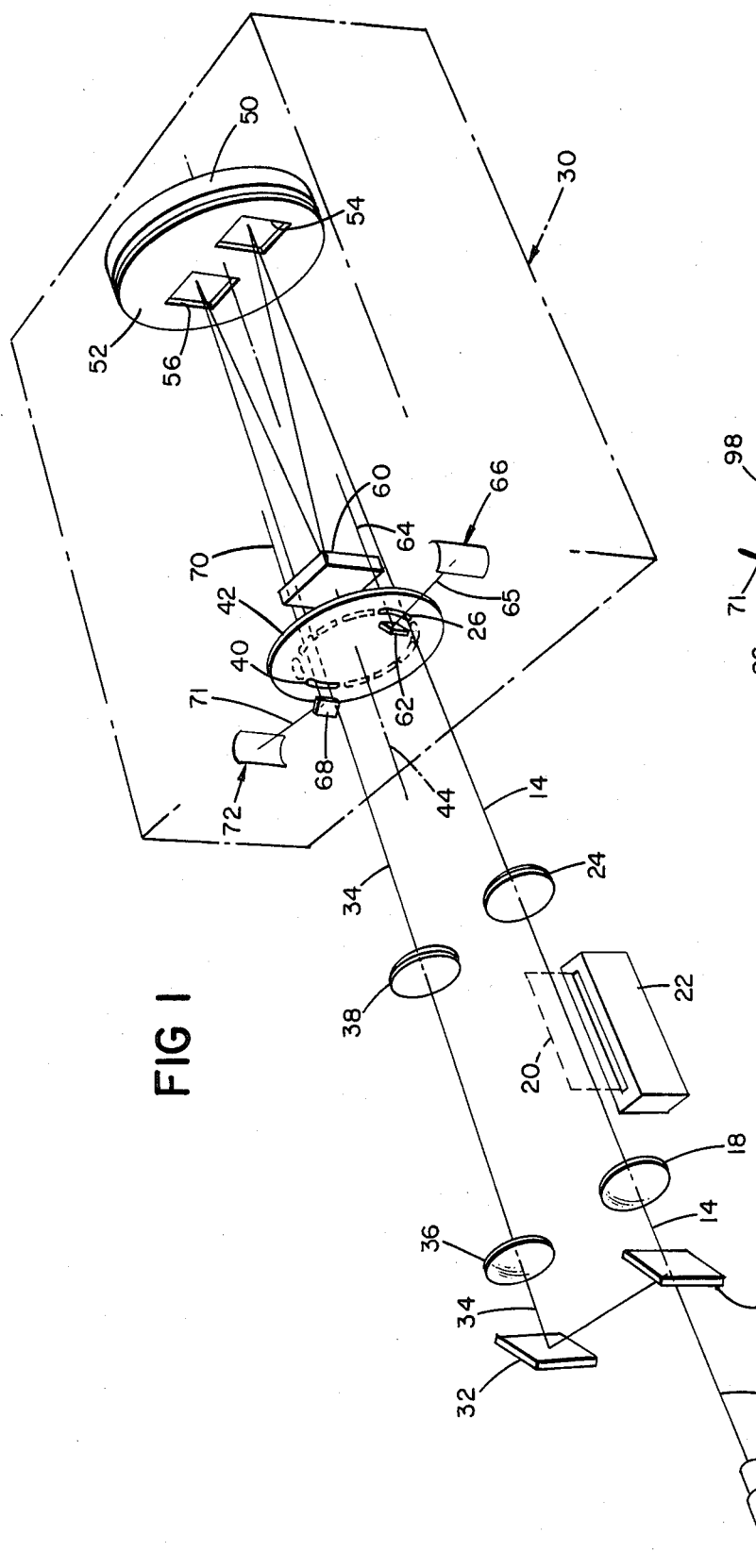
FIG. 1 is a diagram of a spectroanalysis system in accordance with the invention.

The spectroanalytical system shown in the diagram of FIG. 1 includes radiation source 10 in the form of a hollow cathode tube that generates a beam of radiation along part 12. A first (analytical) portion 14 of the radiation in beam 12 from tube 10 is passed through quartz beam splitter 16 and is focused by spherical quartz lens 18 for passage through analysis zone (flame 20 from burner 22) so that the image of the aperture of tube 10 is located in the center of flame 20. A second lens 24 focuses the beam of radiation that passes through flame 20 on the entrance slit 26 of stigmatic monochromator 30. Beam splitter 16 and mirror 32 reflect a second (reference) portion of the output beam 12 along path 34 through lenses 36, 38 for passage through a second entrance slit 40 of monochromator 30.

In this embodiment, slits 26 and 40 are two of a series of ten slits of graduated width that are formed in planar disc 42 of the type shown in Smith et al., U.S. Pat. No. 3,508,813. In this embodiment, disc 42 comprises a copper substrate in which apertures are formed and that carries a nickel film in which five pairs of matched slits are formed along a circle that is about 6.8 centimeters in diameter, the slits being of equal length (about 1.7 centimeters), and graduated in width from ten microns to four-hundred microns to permit slit width adjustability by rotation of disc 42. It will be apparent, of course, that other slit arrangements may be used.

Monochromator 30 includes collimating mirror 50 with an aligned mask 52 that has aperture 54 aligned with the analysis beam 14 of radiation that passes through the lower portion of slit 26 and aperture 56 aligned with the reference beam 34 of radiation that passes through the lower portion of slit 40; and a dispersing element 60 in the form of a reflection grating mounted for rotation about an axis perpendicular to axis 44 of the monochromator. Dispersed radiation from reference beam 34 exits along path 64 through the upper portion of slit 26 and is reflected by mirror 62 mounted adjacent the upper portion of slit 26 along path 65 to photosensor 66. Similarly, dispersed radiation from analysis beam 14 exits along path 70 through the upper portion of slit 40 and is reflected by mirror 68 mounted adjacent the upper portion of slit 40 along path 71 to sensor 72.

Further understanding of the spectroanalytical system may be had with reference to FIGS. 2 and 3. Monochromator 30 is of the Ebert type and of $\frac{1}{3}$ meter focal length. The entrance beams 14, 34 are each located at an angle of twelve minutes below the monochromator axis 44 and the exit beams 64, 70 are similarly each located at a corresponding similar angle above the monochromator axis 44 as indicated in FIG. 3. The beams 14 and 34 are spaced about nine centimeters apart at beam splitter 16 and mirror 32. Each mirror 62, 68 is mounted on a support 74, 76 respectively that is fastened to housing 78 for slit disc 42. Thus, analysis beam 14 enters monochromator 30 through the lower part of slit 26 and, after dispersion, exits in beam 70 through the upper part of slit 40 for sensing by photomultiplier tube 72, as indicated in FIG. 3. Similarly, reference beam 34 enters monochromator 30 through the lower part of slit 40 and a correspondingly dispersed component (beam 64) exits through the upper portion of slit 26 for concurrent sensing by photomultiplier tube 66.

Figure 4:
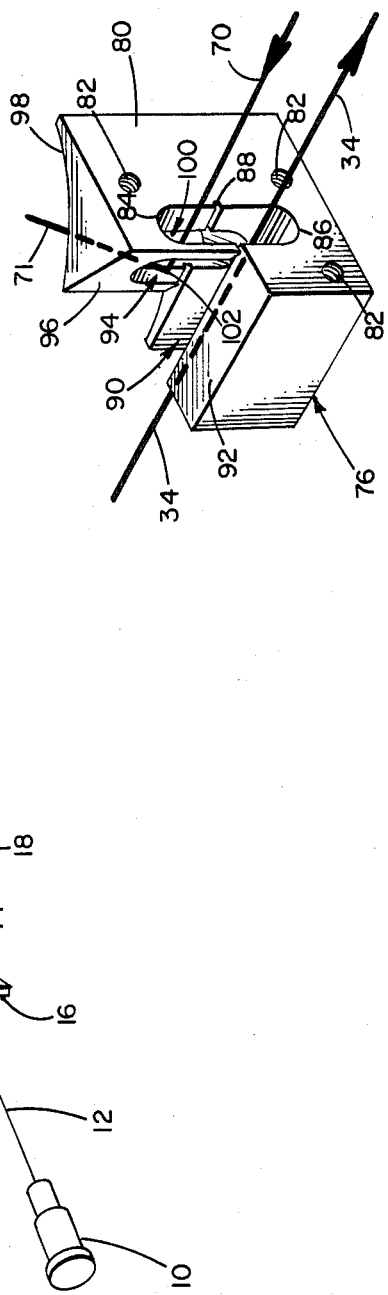
FIG. 4 is a perspective view of a mirror and sensor support that is mounted at the entrance - exit slit 40 of the system shown in FIGS. 1-3.

Further details of the support member 76 for mirror 68 may be seen with reference to the perspective view of FIG. 4. That member provides coordinated support for mirror 68 and photomultiplier tube 72 in accurate alignment with slit 40. A horizontal baffle plate (not shown in FIG. 4) is disposed between entrance beam 34 and exit beam 70. Mirror 62 and photomultiplier tube 66 are accurately positioned relative to slit 26 by a similar support member 74. Each support member 74, 76 is of aluminum and has a planar face 80 that is fastened against a face of housing 78 by fasteners which are received in threaded holes 82, face 80 having a height of about three centimeters and a width of about three centimeters. Formed in face 80 is an elongated opening that has an upper portion 84, a lower portion 86 and a slot 88 that is about 0.8 millimeter in width. Each opening 84, 86 has a width of about 0.6 centimeter and a height of about one centimeter. Channel 90 extends rearwardly from opening 86 through support 76 (a length of about $2\frac{1}{2}$ centimeters) to the rear surface and provides a passage for entrance beam 34. A baffle plate (not shown in FIG. 4) has one edge received in slot 88 and is seated on surface 92 to define the upper boundary of channel 90.

A similar channel 94 extends rearwardly from upper opening 84 to surface 96 that is disposed at an angle of sixty degrees to face 80 and against which mirror 68 is fastened. Cylindrical surface 98 of about two centimeters radius is formed in the rear of block 76 and photosensor 72 is seated against that surface. A third channel 100 extends from channel 94 to the curved surface 98 along a path that is disposed in an angle of thirty degrees to face 80 and provides a path for the exit beam 71 (reflected at 102 by mirror 68) to sensor 72.

In use, the beam of radiation from tube 10 is divided by beam splitter 16 into analysis beam 14 and reference beam 34. The beams 14, 34 are directed along similar paths (analysis beam 14 passing through burner flame 20) and the beams pass through the lower portions of entrance slit 26, 40 respectively. Each beam is collimated by mirror 50 and dispersed into a spectrum by grating 60 with a portion of each resulting spectrum being directed along an exit path 70, 64 respectively through the upper portions of slits 40, 26 respectively, and then reflected by its respective mirror 68, 62 for concurrent sensing by the respective photomultipliers 72, 66. Thus, there is provided a double beam spectroanalytical system that does not require a chopper mechanism.

While a particular embodiment of the invention has been shown and described, various modifications will be apparent to those skilled in the art and therefore it is not intended that the invention be limited to the disclosed embodiment or to details thereof and departures may be made therefrom within the spirit and scope of the invention.

What is claimed is:

1. A spectroanalytical system with compensation for source intensity fluctuations or the like comprising
   means defining an analysis region,
   a radiation source,
   means for passing a first portion of radiation from said radiation source along a first (analysis) beam path through said analysis region for modification by sample material in said analysis region and for passing a second portion of radiation from said beam along a similar second (reference) beam path outside said analysis region,
   a monochromator with two spaced aperture regions, said aperture regions being disposed in a plane that is perpendicular to the axis of said monochromator and arranged such that an entrance aperture for the analysis beam and an exit aperture for a dispersed portion of the reference beam is provided in one aperture region and an entrance aperture for the reference beam and an exit aperture for a dispersed portion of the analysis beam is provided in the other aperture region, the apertures in each said aperture regions being defined by an elongated slit, and said monochromator being arranged such that radiation in each beam enters the monochromator adjacent one end of each slit and dispersed radiation from that beam exits the monochromator adjacent the opposite end of the other slit, said analysis beam and said dispersed portion of said analysis beam defining a first plane that passes through the axis of said monochromator and said reference beam and said dispersed portion of said reference beam defining a second plane that passes through the axis of said monochromator, said first plane being disposed at an angle to said second plane, and
   detector means for sensing radiation that emerges from said exit apertures for providing an indication of the effect of a sample in said analysis region on the radiation from said radiation source.

2. The system of claim 1 wherein said monochromator is of the stigmatic type.

3. The system of claim 1 wherein said radiation source is of the line source type.

4. The system of claim 1 wherein said analysis region is defined by an atomic absorption type burner.

5. The system of claim 1 and further including a mirror supported adjacent the exit beam portion of each aperture region for reflecting radiation onto an associated sensor of said detector means.

6. The system of claim 1 and further including support structure adjacent the exit aperture portion of each said aperture region through which the beam of dispersed radiation passes, each said support structure supporting a photosensor type of detector means and a mirror for reflecting radiation in said beam of dispersed radiation onto said photosensor.

7. The system of claim 1 wherein said analysis and reference beam paths lie in a plane that is angularly offset from the axis of said monochromator.

8. The system of claim 7 wherein the angular offset of said plane from the axis of said monochromator is less than one degree.

9. The system of claim 8 wherein said monochromator is of the stigmatic type, and said slits are curved.

10. The system of claim 9 wherein said monochromator includes a reflection grating and a collimating mirror disposed to concurrently collimate radiation in said analysis and reference beams path for impingement on said reflection grating.

11. A spectroanalytical system comprising
means defining an analysis region,
a radiation source,
means for passing a first portion of radiation from said radiation source along a first (analysis) beam path through said analysis region for modification by sample material in said analysis region and for passing a second portion of radiation from said beam along a similar second (reference) beam path outside said analysis region,
a monochromator system that has a collimating element and a dispersing element, first and second slits symmetrically located with respect to the axis of the monochromator system,
said monochromator being arranged such that one slit functions as an entrance aperture for the analysis beam and an exit aperture for a dispersed portion of the reference beam and the other slit functions as an entrance aperture for the reference beam and an exit aperture for a dispersed portion of the analysis beam,
said analysis beam and said dispersed portion of said analysis beam defining a first plane that passes through the axis of said monochromator and said reference beam and said dispersed portion of said reference beam defining a second plane that passes through the axis of said monochromator, said first plane being disposed at an angle to said secnd plane, and
detector means for simultaneously sensing radiation that emerges from each of the slits for providing an indication of the effect of a sample in said analysis region on the radiation from said radiation source.

12. The system of claim 11 wherein each slit is of elongated configuration, said slits are disposed in a plane perpendicular to said monochromator axis, and said monochromator is arranged such that radiation in each beam enters the monochromator adjacent one end of each slit and dispersed radiation from that beam exits the monochromator adjacent the opposite end of the other slit.

13. The system of claim 12 and further including support structure adjacent said opposite end of each slit through which the beam of dispersed radiation passes, each said support structure supporting a photosensor type of detector means and a mirror for reflecting radiation in said beam of dispersed radiation onto said photosensor.

14. The system of claim 13 wherein said radiation source is of the line source type and each said photosensor is a photomultiplier tube.

15. The system of claim 14 wherein said analysis and reference beam paths lie in a plane that is angularly offset from the axis of said monochromator.

16. The system of claim 15 wherein said monochromator is of the stigmatic type, said slits are curved, said dispersing element is a reflection grating mounted for rotation about an axis perpendicular to said monochromator axis and said collimating element is a mirror arranged to concurrently collimate radiation in said analysis and reference beams path for impingement on said reflection grating and to reflect radiation dispersed by said grating through said slits for reflection by said mirrors to said photomultiplier tubes.

17. The system of claim 16 wherein said radiation source is a hollow cathode lamp and said analysis region is defined by an atomic absorption type burner.

18. The system of claim 17 and further including means to adjust the widths of said slits.

* * * * *